US008182691B2

United States Patent
Stahl

(10) Patent No.: US 8,182,691 B2
(45) Date of Patent: May 22, 2012

(54) APPARATUS FOR EXTRACORPOREAL BLOOD TREATMENT WITH A DEVICE FOR CHECKING A STERILE FILTER, AND METHOD OF CHECKING A STERILE FILTER OF AN EXTRACORPOREAL BLOOD TREATMENT APPARATUS

(75) Inventor: Thomas Stahl, Esselbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1006 days.

(21) Appl. No.: 10/877,189

(22) Filed: Jun. 24, 2004

(65) Prior Publication Data

US 2005/0011833 A1 Jan. 20, 2005

(30) Foreign Application Priority Data

Jun. 25, 2003 (DE) .................................. 103 28 435

(51) Int. Cl.
  *B01D 61/00* (2006.01)
  *B01D 61/32* (2006.01)
  *B01D 63/00* (2006.01)

(52) U.S. Cl. .......... 210/646; 210/739; 210/746; 210/85; 210/103; 210/321.6; 210/321.71; 210/647; 210/650; 604/6.09

(58) Field of Classification Search .................. 210/646
See application file for complete search history.

(56) References Cited

U.S. PATENT DOCUMENTS

| | | | | | |
|---|---|---|---|---|---|
| 5,656,248 | A | * | 8/1997 | Kline et al. | 422/295 |
| 6,039,877 | A | * | 3/2000 | Chevallet et al. | 210/636 |
| 6,187,207 | B1 | * | 2/2001 | Brauer | 210/739 |
| 6,548,017 | B2 | * | 4/2003 | Krivitski et al. | 422/44 |
| 6,607,697 | B1 | * | 8/2003 | Müller | 422/44 |
| 7,033,539 | B2 | * | 4/2006 | Krensky et al. | 422/44 |
| 2002/0043487 | A1 | * | 4/2002 | Schick | 210/85 |

FOREIGN PATENT DOCUMENTS

| | | |
|---|---|---|
| EP | 0930080 A1 * | 1/1999 |
| EP | 0 930 080 | 7/1999 |
| EP | 0 974 371 | 1/2000 |
| EP | 1 170 023 | 1/2002 |

* cited by examiner

*Primary Examiner* — Benjamin Kurtz
(74) *Attorney, Agent, or Firm* — Kenyon & Kenyon LLP

(57) ABSTRACT

An apparatus for extracorporeal blood treatment has a dialysis fluid circuit and a blood circuit which are separated by a dialyzer. Arranged in the dialysis fluid circuit there is a sterile filter for producing a sterile dialysis fluid which flows into the dialyzer. To check the sterile filter, a chemical and/or physical property of the dialysis fluid, for example the conductivity, is changed upstream of the sterile filter, and the change in the property of the dialysis fluid is detected downstream of the sterile filter. From the time shift between the initiation of the conductivity impulse and the detection of the latter, it is possible to tell whether the blood treatment apparatus is fitted with a sterile filter. Moreover, the volume of the sterile filter can be inferred from the length of the time shift.

12 Claims, 2 Drawing Sheets

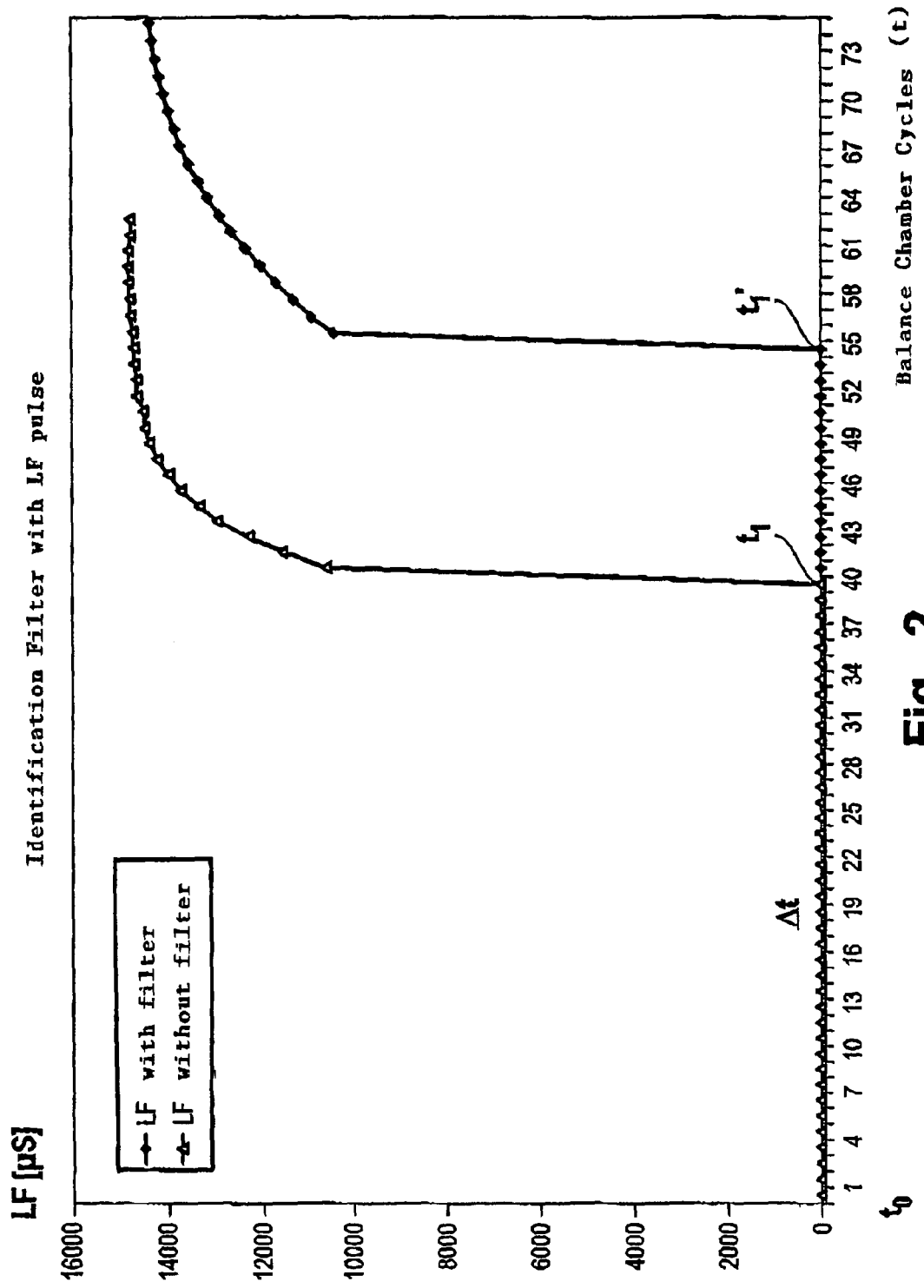

APPARATUS FOR EXTRACORPOREAL BLOOD TREATMENT WITH A DEVICE FOR CHECKING A STERILE FILTER, AND METHOD OF CHECKING A STERILE FILTER OF AN EXTRACORPOREAL BLOOD TREATMENT APPARATUS

FIELD OF THE INVENTION

The invention relates to an apparatus for extracorporeal blood treatment, with a device for checking a sterile filter which is arranged in a dialysis fluid circuit of the blood treatment apparatus. The invention further relates to a method of checking a sterile filter, arranged in a dialysis fluid circuit of an apparatus for extracorporeal blood treatment, before the start of the extracorporeal blood treatment.

BACKGROUND

It is known to produce a dialysis fluid on-line from fresh water and one or more concentrates. The fresh water generally contains no microorganisms and the concentrates are normally sterile, but it is nevertheless difficult to guarantee that the dialysis fluid produced on-line always meets the very stringent sterility requirements imposed in extracorporeal blood treatments.

In hemodiafiltration, it is known to produce a substitution fluid on-line from a dialysis fluid. The substitution fluid in particular should satisfy the stringent requirements concerning sterility.

In order to enable the sterility of the dialysis fluid and substitution fluid, known blood treatment apparati contain sterile filters, which can be replaced after one use or after they have been used several times. European Patent No. EP 0 930 080 A1 describes a blood treatment apparati which has a first sterile filter for producing a sterile dialysis fluid from fresh water and from a dialysis fluid concentrate, and a second sterile filter for producing a sterile substitution fluid from the dialysis fluid. Both sterile filters are arranged in the dialysis fluid circuit upstream of the dialyzer and are flushed with the dialysis fluid.

In practice it is desirable that a sterile filter provided for a blood treatment apparatus is actually fitted in the apparatus. Otherwise there is a risk that the dialysis fluid and/or substitution fluid may not be sterile. Automatic detection of whether the apparatus is fitted with a filter typically requires additional equipment and costs.

SUMMARY OF THE INVENTION

It is therefore an object of the invention to provide an apparatus for extracorporeal blood treatment which permits checking of the sterile filter with relatively little additional equipment. A further object of the invention is to provide a method which permits checking a sterile filter of an extracorporeal blood treatment apparatus and which requires only relatively little outlay in terms of equipment.

According to one embodiment of the present invention, a sterile filter is checked based on determining the time interval between a change in a physical and/or chemical property of the dialysis fluid, initiated in the dialysis fluid circuit upstream of the sterile filter, and the detection of the change in the property of the dialysis fluid in the dialysis fluid circuit downstream of the sterile filter. From the length of the determined time interval, it is then concluded whether the blood treatment apparatus is fitted with a sterile filter. For this purpose, the length of the determined time interval is compared to one or more predefined reference values which are representative of one sterile filter or of various sterile filters of different configurations. In another embodiment, instead of a time interval, a parameter correlating with the time interval, for example the balance chamber cycles, can also be evaluated if the blood treatment apparatus has a balance device with balance chambers.

If the blood treatment apparatus is not fitted with a sterile filter, e.g., the connection terminals of the sterile filter are bridged by a tube line, an impulse-type change in the physical and/or chemical properties of the dialysis fluid initiated upstream of the sterile filter requires a shorter propagation time in order to be able to be detected downstream of the sterile filter than if the blood treatment apparatus is fitted with a sterile filter. This may be attributed to the different volume of dialysis fluid in the predefined section of the dialysis fluid circuit, without or with sterile filter.

One advantage of an apparatus according to one embodiment of the present invention and of the method according to one embodiment of the invention is that additional sensors on the sterile filter itself may not be necessary. Thus, the outlay in terms of equipment may be reduced. Checking of the sterile filter can be carried out before the actual dialysis treatment. The treatment thus may begin when it has been ascertained that the blood treatment apparatus is fitted with the sterile filter. For checking the sterile filter, it may be immaterial whether the dialysis fluid, whose chemical and/or physical property is changed, flows through only the first chamber or the second chamber or through both chambers. For this reason, the sterile filter can also be checked when it is connected into the circuit only for tangential flushing.

The physical and/or chemical property of the dialysis fluid can be any parameter which is detectable in the dialysis fluid. The physical and/or chemical property is preferably the concentration of a defined substance in the dialysis fluid. However, the physical and/or chemical property can also be, for example, the temperature, density or pressure. The measurement of the concentration of a defined substance in the dialysis fluid, for example Na, is preferably done by measuring the electrical conductivity of the dialysis fluid. In measuring the conductivity, it is advantageous that use can be made of conductivity sensors already provided in the dialysis fluid circuit of the blood treatment apparatuses.

To check the sterile filter, it may be sufficient for the physical and/or chemical property of the dialysis fluid to be changed, not constantly, but instead only for brief periods. The property of the dialysis fluid is preferably changed abruptly only for a short time interval. In a particularly preferred embodiment of the invention, the change in the physical and/or chemical property of the dialysis fluid is effected by changing the mixing ratio of water and concentrate(s), preferably only for a short time, during preparation of the dialysis fluid.

In addition to checking that the blood treatment apparatus is fitted with a sterile filter, the apparatus and method according to the invention also make the checking of whether the blood treatment apparatus is fitted with a sterile filter of the correct size. Checking the size of the sterile filter is preferably done by determining the volume of dialysis fluid which flows through the predefined section of the dialysis fluid circuit until the change in the physical and/or chemical property of the dialysis fluid can be detected. This volume is dependent on the volume of the sterile filter through which dialysis fluid flows in the predefined section of the dialysis fluid circuit. Comparison of the determined volume and predefined reference values, which are representative of the various types of sterile filters of different size, permits identification of the respective sterile filter.

In a blood treatment apparatus having a balance device fresh dialysis, fluid may be balanced against used dialysis fluid. The balance device may have at least one balance chamber in which, in successive balance chamber cycles, a predetermined amount of dialysis fluid is conveyed in each case. In this arrangement, the volume of dialysis fluid is advantageously determined from the number of balance chamber cycles and from the predetermined amount of dialysis fluid.

BRIEF DESCRIPTION OF THE DRAWINGS

One embodiment of the invention is explained in more detail below with reference to the drawings, in which:

FIG. 2 shows the conductivity of the dialysis fluid as a function of time, with and without sterile filter, according to one embodiment of the present invention.

DETAILED DESCRIPTION

Figure 1:
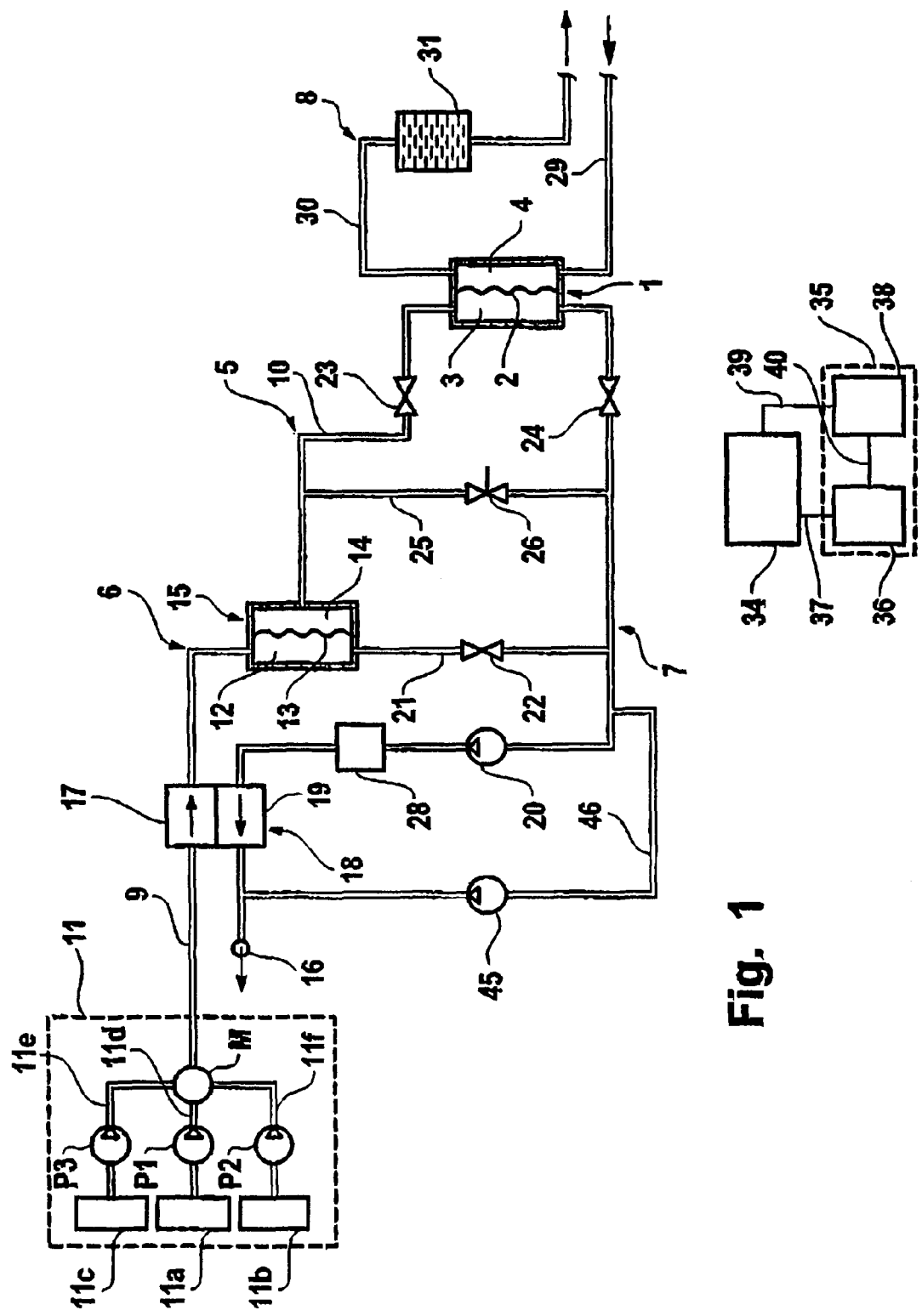
FIG. 1 shows a very much simplified, diagrammatic representation of the main structural components of a hemodialysis apparatus with a device for checking the sterile filter, according to one embodiment of the present invention.

In FIG. 1, the main structural components of a hemodialysis apparatus according of one embodiment are shown in a simplified diagrammatic representation. The dialysis apparatus has a dialyzer 1 which is divided by a semipermeable membrane 2 into a first chamber 3, through which dialysis fluid flows, and a second chamber 4 through which blood flows. The first chamber 3 is coupled into a dialysis fluid circuit 5, which has a dialysis fluid admission line 6 and a dialysis fluid discharge line 7, while the second chamber of the dialyzer 1 is coupled into a blood circuit 8.

The dialysis fluid admission line 6 of the dialysis fluid circuit 5 has a first line section 9 and a second line section 10. The first line section 9 connects a device 11, for preparing dialysis fluid, to the inlet of a first chamber 12 of a sterile filter 15 which is divided into the first chamber 12 and a second chamber 14 by a membrane 13 that filters microorganisms. The second admission section 10 connects the outlet of the second chamber 14 of the sterile filter 15 to the inlet of the first chamber 3 of the dialyzer. The outlet of the first chamber 3 of the dialyzer 1 is connected to an outflow 16 via the dialysis fluid discharge line 7.

The device 11 for preparing fresh dialysis fluid has a freshwater source 11a and two dialysis fluid concentrate sources 11b and 11c. The water source 11a is connected via a water line 11d, and the concentrate sources 11b, 11c via concentrate lines 11e and 11f, to a mixing point M from which the dialysis fluid admission line 9 issues. Proportioning pumps P1, P2 and P3 are coupled into the water and concentrate lines, the flow rates of the pumps being used to set the mixing ratio of water and concentrates for mixing the dialysis fluid.

To balance fresh dialysis fluid against used dialysis fluid, a balance device 18 in employed which is designed as a balance chamber and which has first and second subsidiary chambers 17, 19. The first subsidiary chamber 17 is coupled into the first line section 9 of the dialysis fluid admission line 6, while the second subsidiary chamber 19 is coupled into the dialysis fluid discharge line 7. Upstream of the second subsidiary chamber 19, a dialysis fluid pump 20 is coupled into the dialysis fluid discharge line. In practice, a second balance chamber operating in counter-phase may be used parallel to the first balance chamber 18 in order to permit an almost continuous flow. For reasons of clarity, however, the second balance chamber has not been shown.

From the outlet of the first chamber 12 of the sterile filter 15, a first bypass line 21, into which a first bypass valve 22 is coupled, leads to the dialysis fluid discharge line 7 upstream of the dialysis fluid pump 20. A first shut-off member 23 is arranged upstream of the dialyzer 1 in the second line section 10 of the dialysis fluid admission line 6, and a second shut-off member 24 is arranged downstream of the dialyzer in the dialysis fluid discharge line 7. A second bypass line 25, into which a second bypass valve 26 is coupled, connects the second line section 10 of the dialysis fluid admission line 6 upstream of the first shut-off member 23 to the dialysis fluid discharge line 7 downstream of the second shut-off member 24.

A device 28 for measuring the conductivity of the dialysis fluid is coupled into the dialysis fluid discharge line 7 downstream of the first and second bypass lines 21, 25 and downstream of the dialysis fluid pump 20. Downstream of the first bypass line 21 and upstream of the dialysis fluid pump 20, an ultrafiltration line 46 branches off from the dialysis fluid discharge line 7 and opens into the dialysis fluid discharge line downstream of the second subsidiary chamber 19. An ultrafiltration pump 45 is coupled into the ultrafiltration line 46.

The blood circuit 8 has an admission line 29 coming from the patient and connected to the inlet of the second chamber 4 of the dialyzer 1. The outlet of the second chamber 4 of the dialyzer 1 leads to the patient via a blood discharge line 30 to which a drip chamber 31 is connected.

The dialysis apparatus also has a central control unit 34 which, via control lines (not shown), controls the dialysis fluid pump and ultrafiltration pump 20, 45, the proportioning pumps P1, P2, P3, the shut-off members 22, 23, 24 and 26, and the balance device 18.

During the dialysis treatment, the first and second shut-off members 23, 24 are opened and the first and second bypass valves 22, 26 are closed, so that dialysis fluid flows from the device 11, for preparing dialysis fluid, via the first subsidiary chamber 17 of the balance device 18 and via the sterile filter 15 into the first subsidiary chamber 3 of the dialyzer. From the first chamber of the dialyzer, the dialysis fluid then flows to the outflow 16 via the second subsidiary chamber 19 of the balance device 18. The sterile filter 15 provides for sterile dialysis fluid to reach the dialyzer 1.

For flushing the sterile filter 15, the first and second shut-off members 23, 24 are closed and the first bypass valve 22 is opened, so that the dialysis fluid runs off directly into the outflow 16. With the second bypass valve 26 opened, the second bypass line 25 serves to circumvent the dialyzer after flushing mode with the first and second shut-off members 23, 24 closed. Here once again, the dialysis fluid flows directly into the outflow 16.

The sterile filter 15 may be used one or more times and can be replaced while the lines are disconnected. A device 35 for checking the sterile filter determines that the dialysis apparatus is fitted with a sterile filter at the start of the actual dialysis treatment. The device 35 for checking the sterile filter 15 has a computing unit 36 which is connected via a data line 37 to the central control unit 34 and via a data line 40 to an alarm unit 38, which emits an acoustic and/or visual alarm. The alarm unit 38 is in turn connected via a data line 39 to the control unit 34 which, in the event of an alarm, interrupts the routine of preparing for the dialysis treatment in order to fit the dialysis machine with a sterile filter.

During the routine of preparing for the dialysis treatment, the device 35 checks the sterile filter in the following way:

First, the dialysis fluid circuit 6 is flushed with fresh water. At this stage, only the proportioning pump P1 is in operation, not the pumps P2 and P3. Then one of the two pumps P2 and P3 is triggered briefly to generate a concentrate bolus, which can be detected as a conductivity impulse in the dialysis fluid. This conductivity impulse propagates through the dialysis fluid admission line 6 (which includes the sterile filter 15), the dialyzer 1 and the dialysis fluid discharge line 7 until it reaches the device 28 for measuring the conductivity of the dialysis fluid and is detected.

The computing unit 36 is configured to determine the time interval $\Delta t$ between the first time, at which the conductivity impulse is generated by the device 11 for preparing the dialysis fluid, and the second time, at which the conductivity impulse is detected by the device 28 for measuring the conductivity. The computing unit 36 is also configured to compare the length of the time interval $\Delta t$ to predefined reference values which are representative of the sterile filters 15 used. The time t, at which the measurement starts, can be defined by any desired signals associated with the development of the change in the property, for example the conductivity impulse. A further conductivity sensor can be provided for detection of the conductivity impulse at a certain point on the measurement length to the time of the start of the measurement.

FIG. 2 shows the conductivity of the dialysis fluid as a function of time, the time axis being given in balance chamber cycles. Since the balance device 18, in successive balance chamber cycles, delivers in each case a predetermined amount of dialysis fluid, there may be a fixed predefined relationship between the volume of dialysis fluid delivered and the number of balance chamber cycles. In the present example, a dialysis fluid flow rate of 500 ml/min has been set, with a balance chamber cycle of 3.3 seconds duration. In the present illustrative embodiment, a balance chamber filling is 30 m/l. Thus, for example, 15 balance chamber cycles correspond to a time shift of 49.5 seconds and a volume difference of 450 ml.

FIG. 2 shows that the conductivity impulse initiated at the time t=0 can be detected at the time $t=t_1$ after a time shift $\Delta t$ of 132 s, corresponding to 40 balance chamber cycles, if the dialysis apparatus is not fitted with a sterile filter 15. If the dialysis apparatus is fitted with a sterile filter 15, the conductivity impulse is not detected until the time $t=t_1'$ after 55 balance chamber cycles, i.e. 181.5 seconds. Here, the conductivity impulse is detected by detection of the abrupt rise in conductivity.

In the computing unit 36, the number of balance chamber cycles corresponding to the time shift is compared to a predefined reference value lying between 40 and 55 balance chamber cycles, for example 50 balance chamber cycles. In the event that the determined time shift is smaller than the reference value, the computing unit 36 sends an alarm signal to the alarm unit 38, which emits an acoustic and/or visual alarm and, via the control unit, interrupts the routine of preparing for the dialysis treatment.

The time shift $\Delta t$ may be dependent on the volume of the dialysis fluid flowing through the predefined section of the dialysis fluid circuit that includes the sterile filter. A sterile filter with a greater volume may consequently cause a greater time shift than a sterile filter with a smaller volume.

To identify a sterile filter with a specified volume, the computing unit compares the time shift to predefined limit values which are each characteristic of a sterile filter with a specified volume. If the time shift is greater than the respective characteristic limit value, it may be concluded that the respective sterile filter is used.

In the illustrative embodiments described, the sterile filter 15 may be checked both with fluid flowing through the dialyzer 1 and also with fluid flowing through the first or second bypass line 21, 25, because the device 28 for measuring the conductivity is arranged downstream of the first and second bypass lines 21, 25. However, the device 28 can also be arranged in the second section of the dialysis fluid admission line 10. Then, however, it may be difficult to check the sterile filter with fluid flowing through the first bypass line 21. On the other hand, the predefined volume enclosed by the sterile filter in such an arrangement of the device 28 is smaller, because part of the dialysis fluid admission and discharge lines is omitted. At the same time, the reference values to be used may change. When measuring via the bypass line 21, it may be noted in particular that dialysis fluid flows through one chamber of the sterile filter 15.

What is claimed is:

1. An apparatus for extracorporeal blood treatment comprising:
    a dialysis fluid preparation device for preparing fresh dialysis fluid, adapted to change at least one of a chemical and a physical property of the dialysis fluid;
    a filter divided into a first filter chamber and a second filter chamber by a membrane for filtering microorganisms, the filter located downstream from the dialysis fluid preparation device;
    a measuring device for measuring a change in the at least one of the chemical and physical property of the dialysis fluid, the measuring device located downstream from the filter;
    a dialyzer divided by a semi-permeable membrane into a first dialyzer chamber and a second dialyzer chamber, the first dialyzer chamber being arranged in a dialysis fluid circuit and the second dialyzer chamber being arranged in a blood circuit, the dialyzer located downstream from the filter; and
    a computing unit configured to:
    determine at least one reference value representative of a filter being present;
    determine a first time $t_0$ at which the dialysis fluid preparation device changes the at least one of the chemical and physical property of the dialysis fluid;
    determine a second time $t_1$ at which the measuring device detects the change in the at least one of the chemical and physical property of the dialysis fluid;
    determine a time interval $\Delta t$ by subtracting the first time $t_0$ from the second time $t_1$;
    compare the time interval $\Delta t$, or a parameter correlating to the time interval $\Delta t$, to the reference value; and
    determine that a filter is present if the time interval, or a parameter correlating to the time interval, matches the at least one reference value, or determine that a filter is not present if the time interval, or a parameter correlating to the time interval, does not match the at least one reference value.

2. The apparatus as claimed in claim 1, wherein the at least one of the physical and chemical property of the dialysis fluid is a concentration of a defined substance in the dialysis fluid.

3. The apparatus as claimed in claim 1, wherein the measuring device measures the conductivity of the dialysis fluid.

4. The apparatus as claimed in claim 1, wherein
    the dialysis fluid preparation device has a water source and at least one concentrate source and is configured to mix water and concentrate(s), and change the mixing ratio of water and concentrate(s).

5. The apparatus as claimed in claim 1, wherein the computing unit is further configured to:

determine a first time $t_0$, at which the at least one of the physical and chemical property of the dialysis fluid upstream of the filter is changed, and a second time $t_1$, at which the change in the at least one of the chemical and physical property of the dialysis fluid is detected by the measuring device, define a section of the dialysis fluid circuit, and determine a volume V of dialysis fluid flowing through the section of the dialysis fluid circuit between the first time $t_0$ and the second time $t_1$, wherein the parameter correlating to the time interval $\Delta t$ is the volume V.

6. The apparatus as claimed in claim 5, further comprising a balance device for balancing fresh dialysis fluid against used dialysis fluid, said balance device having at least one balance chamber which comprises two subsidiary chambers, wherein the volume of dialysis fluid can be determined from a number of balance chamber cycles and a volume of the at least one balance chamber.

7. The apparatus as claimed in claim 1, wherein the dialysis fluid circuit has a first line section of a dialysis fluid admission line extending from the dialysis fluid preparation device to the inlet of the first filter chamber, and a second line section of the dialysis fluid admission line extending from the second filter chamber to the inlet of the dialyzer, and the dialysis fluid circuit has a dialysis fluid discharge line extending from the outlet of the dialyzer to an outlet of the apparatus, the measuring device being located in the dialysis fluid discharge line.

8. The apparatus as claimed in claim 7, wherein the dialysis fluid circuit has a bypass line extending from an outlet of the first filter chamber to the dialysis fluid discharge line, the measuring device being located downstream of the bypass line.

9. The apparatus of claim 1, further comprising an alarm operatively connected to the computing unit, wherein the computing unit is further configured to activate the alarm if it is determined that a filter is not present.

10. The apparatus of claim 1, wherein when the alarm is activated, the dialysis fluid preparation device is interrupted.

11. The apparatus of claim 9, wherein the alarm is configured to receive a signal if it is determined that a filter is not present.

12. The apparatus of claim 1, wherein the computing unit is further configured to stop the dialysis preparation device if it is determined that a filter is not present.

* * * * *